United States Patent [19]

Aumueller et al.

[11] Patent Number: 4,940,742
[45] Date of Patent: Jul. 10, 1990

[54] 2,6-POLYALKYLPIPERIDINE-SUBSTITUTED BENZIMIDAZOLE-2-CARBOXANILIDES AND THEIR USE FOR STABILIZING ORGANIC MATERIAL

[75] Inventors: Alexander Aumueller, Deidesheim; Peter Spang, St. Ingbert; Peter Neumann, Mannheim; Hubert Trauth, Dudenhofen, all of Fed. Rep. of Germany

[73] Assignee: BASF Aktiengesellschaft, Ludwigshafen, Fed. Rep. of Germany

[21] Appl. No.: 392,598

[22] Filed: Aug. 11, 1989

[30] Foreign Application Priority Data

Aug. 23, 1988 [DE] Fed. Rep. of Germany ....... 3828536

[51] Int. Cl.$^5$ ............................................. C08K 5/3447
[52] U.S. Cl. ........................................ 524/93; 546/199
[58] Field of Search ........................... 546/199; 524/93

[56] References Cited

U.S. PATENT DOCUMENTS

| | | | |
|---|---|---|---|
| 3,661,925 | 5/1972 | McCaully et al. | 548/311 |
| 3,740,413 | 6/1973 | McCaully et al. | 548/311 |
| 3,907,700 | 9/1975 | Grier | 252/589 |
| 4,011,236 | 3/1977 | Grier | 548/306 |

FOREIGN PATENT DOCUMENTS 0284828 10/1988 European Pat. Off.
1517719 2/1968 France.

OTHER PUBLICATIONS

Chemische Berichte, vol. 92, 1959, R. Gompper et al., pp. 550–563.
J. Chem. Soc., Sect. C, 1967, G. Holan et al., pp. 20–25, "2-Trihalogenomethylbenzazoles."
Chemical Abstracts, vol. 101, 1984, p. 594, 23395a.
Chemical Abstracts, vol. 98, 1983, p. 571, 143322r.
Bulletin De La Societe Chimique De France, No. 10, 1966, R. Salle et al., p. 3368.

*Primary Examiner*—Richard A. Schwartz
*Assistant Examiner*—Richard A. Sharpe
*Attorney, Agent, or Firm*—Oblon, Spivak, McClelland, Maier & Neustadt

[57] ABSTRACT

Benzimidazolecarboxanilides of the formula (I)

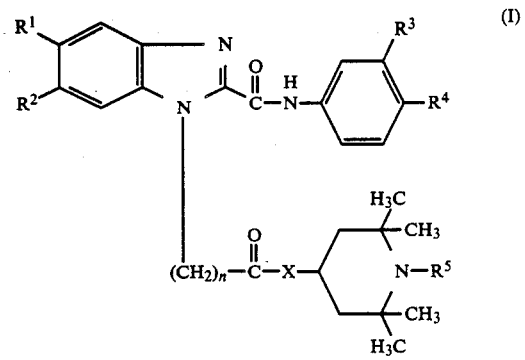

where $R^1$ and $R^2$ independently of one another are each hydrogen, chlorine, bromine, alkyl, alkoxy, unsubstituted or alkyl-substituted or alkoxy-substituted phenyl or phenylalkyl, $R^3$ and $R^4$ independently of one another are each hydrogen, alkyl, alkyl which is interrupted by one or more oxygen atoms, alkoxy, alkoxy which is interrupted by one or more oxygen atoms, unsubstituted or alkyl-substituted or alkoxy-substituted phenyl, phenylalkoxy, alkanoylamino, benzoylamino, alkanoyloxy or benzoyloxy, n is 0, 1, 2, 3, 4 or 5, X is oxygen,

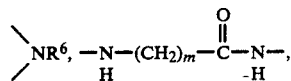

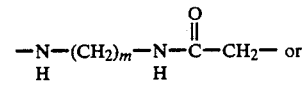

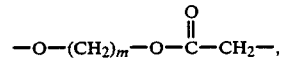

$R^5$ is hydrogen, alkyl, phenylalkyl, cyanomethyl, aminoethyl, hydroxyethyl, alkylcarbonyl or benzoyl, $R^6$ is hydrogen, alkyl, phenylalkyl or phennyl and m is from 2 to 8, and the acid addition salts and hydrates of these compounds are stabilizers for organic material, in particular for plastics, such as polyethylene, polypropylene and polyamide.

17 Claims, No Drawings

2,6-POLYALKYLPIPERIDINE-SUBSTITUTED BENZIMIDAZOLE-2-CARBOXANILIDES AND THEIR USE FOR STABILIZING ORGANIC MATERIAL

It is known that polyalkylpiperidine derivatives protect organic polymers from destruction by light and heat.

In the case of the prior art stabilizers, their compatibility with polyolefins and other plastics, the duration of the protective effect, their volatility and their thermal decomposition during incorporation in the polymers at elevated temperatures are often unsatisfactory.

It is an object of the present invention to provide novel stabilizers which do not have the above disadvantages.

We have found that this object is achieved by a molecular combination of benzimidazolecarboxanilides and polyalkylpiperidine derivatives. The present invention accordingly relates to polyalkylpiperidine-substituted benzimidazolecarboxanilides of the general formula (I)

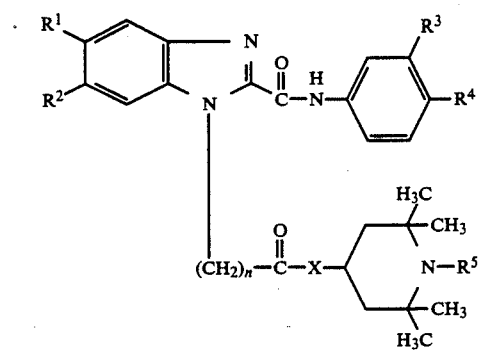

where $R^1$ and $R^2$ independently of one another are each hydrogen, chlorine, bromine, $C_1$-$C_4$-alkyl, $C_1$-$C_4$-alkoxy, or $C_7$-$C_9$-phenylalkyl or phenyl which is unsubstituted or substituted by $C_1$-$C_4$-alkyl or $C_1$-$C_4$-alkoxy, $R^3$ and $R^4$ independently of one another are each hydrogen, $C_1$-$C_{18}$alkyl, $C_3$-$C_{18}$-alkyl which is be interrupted by one or more oxygen atoms, $C_1$-$C_{18}$alkoxy, $C_4$-$C_{18}$alkoxy which is interrupted by one or more oxygen atoms, phenyl which is unsubstituted or substituted by $C_1$-$C_4$-alkyl or $C_1$-$C_4$-alkoxy, or phenyl -$C_1$-$C_8$-alkoxy, $C_1$-$C_{12}$-alkanoylamino, benzoylamino, $C_2$-$C_{12}$-alkanoyloxy or benzoyloxy, n is 0, 1, 2, 3, 4 or 5, X is

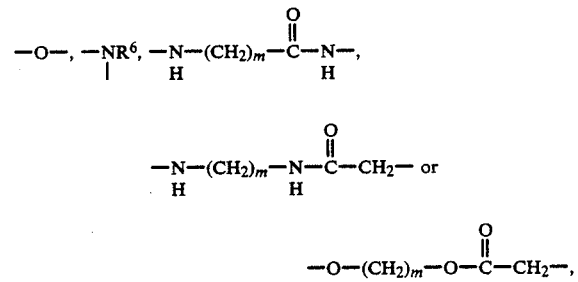

$R^5$ is hydrogen, $C_1$-$C_8$-alkyl, $C_7$-$C_{10}$-phenylalkyl, cyanomethyl, aminoethyl, hydroxyethyl, $C_1$-$C_8$-alkylcarbonyl, formyl or benzoyl, $R^6$ is hydrogen, $C_1$-$C_8$-alkyl, $C_7$-$C_{10}$-phenylalkyl or phenyl and m is from 2 to 8, and the acid addition salts and hydrates of these compounds.

The compounds (I) are very suitable for stabilizing organic material, especially plastics, to degradation by light and heat. They are also effective as metal deactivators. The novel compounds are preferably used for stabilizing polyolefins, in particular ethylene polymers or propylene polymers, and polyurethanes and ABS. (I) is also preferably used for stabilizing polyamides. The compounds (I) are added in an amount of from 0.01 to 5, preferably from 0.02 to 1, % by weight, based on the polymer, to the plastics to be stabilized, before, during or after polymer formation.

Alkyl radicals $R^1$ and $R^2$ are, for example, methyl, ethyl, n-propyl, isopropyl, n-butyl, isobutyl and tertbutyl.

Alkoxy radicals $R^1$ and $R^2$ are, for example, methoxy, ethoxy, n-propoxy, isopropoxy and n-butoxy.

Further radicals $R^1$ and $R^2$ may be, for example, phenyl, tolyl, methoxyphenyl, ethoxyphenyl, benzyl, phenylethyl, phenylpropyl and in particular hydrogen.

Alkyl radicals $R^3$ and $R^4$ are, for example, methyl, ethyl, propyl, butyl, isopropyl, isobutyl, tert-butyl, pentyl, isopentyl, hexyl, heptyl, octyl, nonyl, decyl, undecyl, dodecyl and octadecyl.

Alkoxy radicals $R^3$ and $R^4$ may be, for example, methoxy, ethoxy, n-propoxy, isopropoxy, n-butoxy, isobutoxy, tert-butoxy, pentyloxy, hexyloxy, 2-ethylhexyloxy, heptyloxy, octyloxy, dodecyloxy and octadecyloxy.

Unsubstituted or substituted phenyl radicals $R^3$ and $R^4$ are, for example, phenyl, tolyl, methoxyphenyl, ethoxyphenyl, propoxyphenyl, butoxyphenyl, ethylphenyl, propylphenyl, butylphenyl, isopropylphenyl, isobutylphenyl, tert-butylphenyl, isopropoxyphenyl and isobutoxyphenyl.

Suitable phenylalkoxy radicals $R^3$ and $R^4$ are, for example, benzyloxy, phenylethoxy, phenylpropoxy, phenylbutoxy and phenylnonyloxy.

$R^3$ and $R^4$ may also be phenoxy.

Examples of alkanoylamino radicals $R^3$ and $R^4$ are formylamino, acetylamino, propionylamino, butanoylamino, isobutanoylamino, tert-butanoylamino, pentanoylamino, hexanoylamino, 2-ethylhexanoylamino, heptanoylamino, octanoylamino, nonanoylamino, decanoylamino, dodecanoylamino, octadecanoylamino and benzoylamino.

Alkanoyloxy radicals $R^3$ and $R^4$ are, for example, acetyloxy, propionyloxy, butanoyloxy, isobutanoyloxy, tert-butanoyloxy, pentanoyloxy, hexanoyloxy, 2-ethylhexanoyloxy, heptanoyloxy, octanoyloxy, nonanoyloxy, decanoyloxy, dodecanoyloxy, octadecanoyloxy and benzoyloxy.

Preferred compounds of the formula (I) are those in which $R^3$ is hydrogen and R is hydrogen, methyl, ethyl, propyl, methoxy, propoxy, ethoxy, butoxy, phenoxy, acetylamino or propionylamino.

Particularly preferred compounds of the general formula (I) are those in which R: is hydrogen and R is hydrogen or ethoxy, n is 0, 1, 2, 3, 4 or 5, preferably 1 or 2, and X, in addition to oxygen, may be, for example,

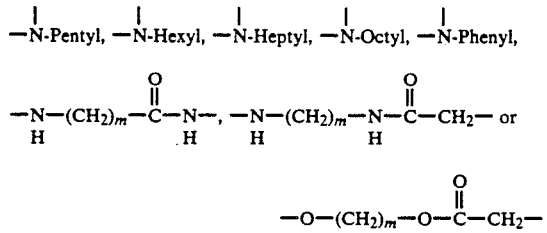

where
m is an integer of from 2 to 8, preferably 2.
X is particularly preferably NH or

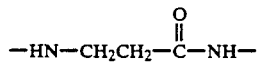

Specific examples of $R^5$ are hydrogen, methyl, ethyl, propyl, butyl, pentyl, hexyl, heptyl, octyl, benzyl, phenylethyl, phenylpropyl, phenylbutyl, cyanomethyl, aminoethyl, hydroxyethyl, formyl, acetyl, propionyl, butanoyl, pentanoyl, hexanoyl, heptanoyl and octanoyl.

$R^5$ is preferably methyl or, in particular, hydrogen.

The compounds of the general formula (I) can be prepared in a conventional manner, for example by reacting a compound of the general formula (II), where R is a lower alkyl radical, e.g. methyl or ethyl, with a compound of the general formula (III):

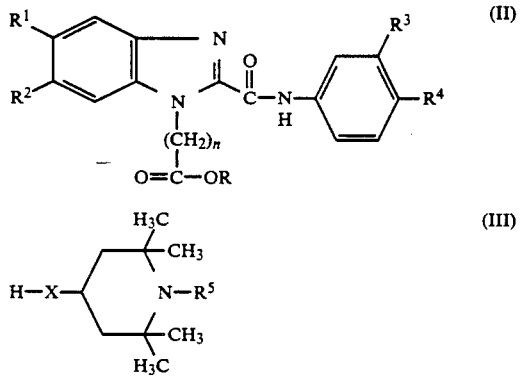

Compounds of the general formula (II) can be prepared, for example, by reacting a compound of the general formula IV with an acrylate, a halocarboxylate or a halocarboxylic acid and then carrying out esterification.

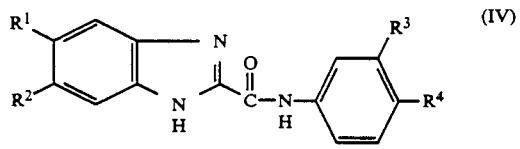

The preparation of the compounds of the general formula (IV) is described in, for example, EP-A-0 284828.

Compounds of the general formula (I) where $R^5$ is H can be converted into compounds of the general formula (I) where $R^5$ is not H by conventional methods, such as alkylation, acylation, reductive amination, cyanomethylation or hydroxyethylation.

The novel compounds may occur in the form of the free bases or as salts. Suitable anions are derived from, for example, inorganic acids and, in particular, from organic carboxylic and organic sulfonic acids.

Examples of inorganic anions are chloride, bromide, sulfate, methosulfate, tetrafluoborate, phosphate and thiocyanate.

Examples of suitable carboxylic acid anions are formate, acetate, propionate, hexanoate, cyclohexanoate, lactate, stearate, dodecylbenzoate, benzoate, acrylate, methacrylate, citrate, malonate and succinate as well as anions of polycarboxylic acids having not more than about 3,000 COOH groups.

Sulfonic acid anions are, for example, benzenesulfonate and tosylate.

The novel compounds (I) can be mixed with the plastics in any known apparatus and by a known method for mixing stabilizers or other additives into polymers.

The plastics stabilized with the novel compounds may contain further additives, for example antioxidants, light stabilizers, metal deactivators, antistatic agents, flame-retarding agents, pigments and/or fillers.

Antioxidants and light stabilizers which may be added to the plastics in addition to the novel compounds are, for example, compounds based on sterically hindered phenols or costabilizers containing sulfur or phosphorus.

Examples of such phenolic antioxidants are 2,6- di-tert-butyl-4-methylphenol, n-octadecyl- β-(3,5-di-tert-butyl-4-hydroxyphenyl)-propionate, 1,1,3-tris-(2-methyl-4-hydroxy-5-tert-butylphenyl)-butane, 1,3,5-trimethyl-2,4,6-tris-(3,5-di-tert-butyl-4-hydroxybenzyl)-benzene, 1,3,5-tris-(3,5-di-tert-butyl-4-hydroxybenzyl) isocyanurate, 1,3,5-tris-[β-(3,5-di-tert-butyl-4-hydroxyphenyl)-propionyloxyethyl]isocyanurate, 1,3,5-tris-(2,6-dimethyl-3-hydroxy-4-tert-butylbenzyl) isocyanurate and pentaerythritol tetrakis-[(3,5-di-tert-butyl-4-hydroxyphenyl)-propionate].

Examples of suitable phosphorus-containing antioxidants are tris-(nonylphenyl) phosphite, distearyl pentaerythritol diphosphite, tris-(2,4-di-tert-butylphenyl) phosphite, tris-(2-tert-butyl-4-methylphenyl) phosphite, bis-(2,4-di-tert-butylphenyl) pentaerythritol diphosphite and tetrakis-(2,4-di-tert-butylphenyl) 4,4′-diphenylene diphosphite.

Examples of sulfur-containing antioxidants are dilauryl thiodipropionate, dimyristyl thiodipropionate, distearyl thiodipropionate, pentaerythritol tetrakis-(β-laurylthiopropionate) and pentaerythritol tetrakis-(β-hexylthiopropionate).

Further antioxidants and light stabilizers which may be used together with the novel compounds are, for example, 2-(2,-hydroxyphenyl)-benzotriazoles, 2-hydroxybenzophenones, aryl esters of hydroxybenzoic acids, α-cyanocinnamic acid derivatives, nickel compounds or oxalic acid dianilides.

Examples of organic polymers which may be stabilized by the novel compounds are: polymers of mono- and diolefins, for example low density or high density polyethylene, linear polybut-1-ene, polyisoprene, polybutadiene and copolymers of mono- or diolefins or mixtures of the stated polymers; copolymers of mono- or diolefins with other vinylmonomers, for example ethylene/alkyl acrylate copolymers, ethylene/alkyl methacrylate copolymers, ethylene/vinyl acetate copolymers or ethylene/acrylic acid copolymers; polystyrene; copolymers of styrene or α-methylstyrene with dienes or acryloyl derivatives, for example styrene/butadiene, styrene/acrylonitrile, styrene/ethyl methacrylate, styrene/butadiene/ethyl acrylate or styrene/acrylonitrile/methacrylate; ABS, MBS or similar polymers; halogen-containing polymers, for example polyvinyl chloride, polyvinyl fluoride, polyvinylidene chloride and their copolymers; polymers which are derived from α,β-unsaturated acids and their derivatives, such as polyacrylates, polymethacrylates, polyacrylamides and polyacrylonitriles; polymers which are derived from unsaturated alcohols and amines or from their acryloyl derivatives or acetals, for example polyvinyl alcohol or polyvinyl acetate; polyurethanes, polyamides, polyureas, polyesters, polycarbonates, polysulfones, polyethersulfones and polyether ketones.

The novel compounds can also be used to stabilize surface coatings, for example industrial coatings. Among these, baking finishes are particularly noteworthy, and among these in turn automotive finishes, preferably two-coat finishes, are particularly noteworthy.

Here too, the abovementioned antioxidants and light stabilizers may also be present.

The novel compounds can be added in solid or dissolved form to the coating. Their good solubility in coating systems is of particular advantage here.

The Examples which follow further illustrate the invention.

EXAMPLE 1

(a) 169 g of 4'-ethoxybenzimidazole-2-carboxanilide, 99.4 g of potassium carbonate and 87 g of methyl chloroacetate in 400 ml of dimethylformamide were stirred for 75 minutes at 90°–95° C. The hot reaction mixture was filtered off under suction and washed with 150 ml of hot dimethylformamide, and the solution was treated with active carbon. After the latter had been filtered off, the clear solution was poured into about 4 l of methanol and stirred for a further hour. The precipitate which separated out was filtered off under suction, washed with methanol and dried. 125 g of the compound of the formula

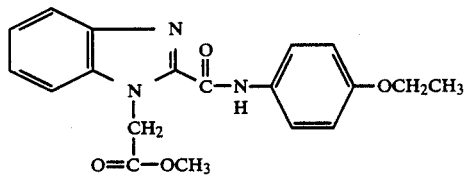

were obtained as a colorless solid of melting point 140°–141° C.

Calculated: C 64.6, H 5.4, N 11.9, 0 18.1. Found: C 64.6, H 5.6, N 11.9, 0 18.0.

(b) 125 g of the product from (a) and 200 ml of 2,2,6,6-tetramethyl-4-aminopiperidine were heated at 130°–135° C. for 5 hours. The hot reaction mixture was stirred into 3.5 l of water, and the precipitate which separated out was filtered off under suction, washed with 500 ml of water and dried. Recrystallization from acetonitrile gave 80.2 g of the compound of the formula

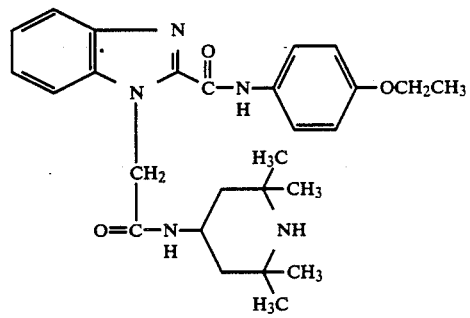

as a colorless solid of melting point 213°–215° C.

Calculated: C 67.9, H 7.4, N 14.5, O 10.0. Found: C 67.8, H 7.6, N 14.5, O 10.2.

EXAMPLE 2

(a) 71.3 g of benzimidazole-2-carboxanilide, 50 g of potassium carbonate and 66.8 g of ethyl bromoacetate in 200 ml of dimethylformamide were heated for 1.5 hours at 90°–95° C. The hot reaction mixture was filtered and the residue was washed with 80 ml of hot dimethylformamide. The combined filtrates were poured into 2.5 l of ethanol. The precipitate which separated out was filtered off under suction, washed with 200 ml of cold ethanol and dried at 90° C. 39.5 g of the compound of the formula

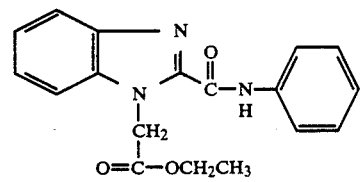

were obtained as a colorless solid of melting point 135°–138° C.

Calculated: C 66.9, H 5.3, N 13.0, O 14.9. Found: C 67.2, H 5.5, N 12.9, O 14.5.

(b) 16.1 g of the product from 2(a) and 100 ml of 2,2,6,6-tetramethyl-4-aminopiperidine were heated for 5 hours at 110°–120° C. and then for 4 hours at 160°–175° C.

Thereafter, the reaction mixture was stirred into 800 ml of water, and the precipitate which had separated out was filtered off under suction, washed with water and dried. Recrystallization from acetonitrile gave 7.3 g of the compound of the formula

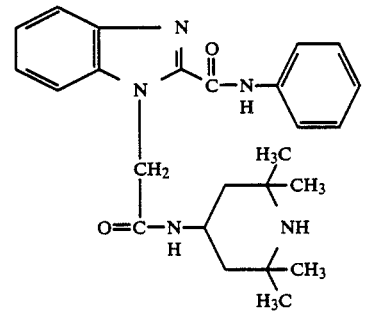

as a colorless solid of melting point 220°–225° C.

Calculated: C 69.3, H 7.2, N 16.1, O 7.4. Found: C 69.5, H 7.0, N 15.5, O 8.1,

EXAMPLE 3

(a) 169 g of 4,-ethoxybenzimidazole-2-carboxanilide, 99.4 g of potassium carbonate and 98 g of methyl 3-chloropropionate in 400 ml of dimethylformamide were heated for 2 hours at 90°–95° C. Working up was effected as in Example 1. Precipitation was carried out in 4 l of methanol and 1,000 g of ice. Filtering off under suction, washing and drying gave 175.9 g of the compound of the formula

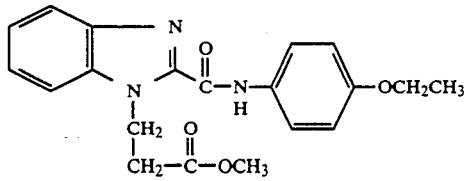

as a colorless solid of melting point 121°–122° C.

Calculated: C 65.4, H 5.7, N 11.4, O 0 17.4. Found: C 65.5, H 5.8, N 11.3, O 17.5.

(b) 36.7 g of the product from 3(a) and 150 ml of 2,2,6,6-tetramethyl-4-aminopiperidine were heated for hours at 130°–135° C. After the addition of 2 ml of a strength methanolic sodium methylate solution, heating was continued for a further 3 hours at 130°–135° C. About 80% of the excess amine were distilled off under reduced pressure from a water pump, the residue was dissolved in 170 ml of methanol, insoluble constituents were filtered off and the solution was poured onto 600 ml of water. The precipitate was filtered off under suction and dried. Recrystallization from toluene gave 30.4 g of the compound of the formula

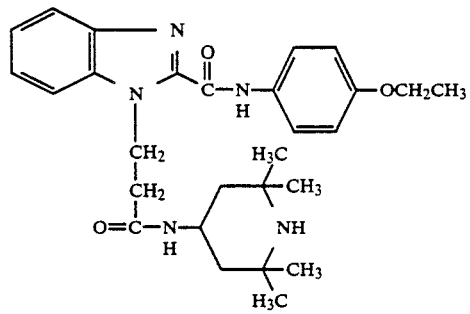

as a colorless solid of melting point 144°–147° C.

Calculated: C 68.4, H 7.6, N 14.2, O 9.8. Found: C 68.8, 'H 7.5, N 13.5, O 9.8.

EXAMPLE 4

(a) 28.3 g of the product from Example 1 and 23.0 g of β-alanine-2,2,6,6-tetramethyl-4-piperidinylamide in ml of ethanol were heated at the boil for 4.5 h with the addition of 36.0 g of 30% strength methanolic sodium methylate solution. The solvent was distilled off under reduced pressure, and the residue was stirred with water, filtered off under suction, washed with water and recrystallized from acetonitrile.

5.8 g of the compound of the formula

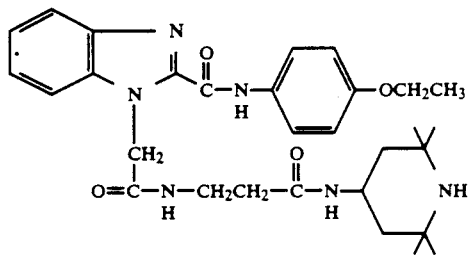

were obtained as a colorless solid of melting point 230° C.

Calculated: C 65.7, H 7.3, O 11.7. Found: C 65.4, H 7.8, O 12.4.

We claim:

1. A benzimidazolecarboxanilide of the formula (I)

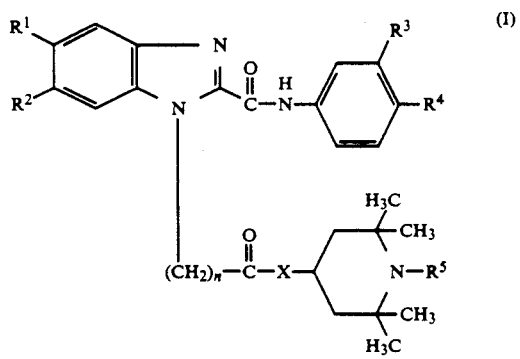

where $R^1$ and $R^2$ independently of one another are each hydrogen, chlorine, bromine, $C_1-C_4$-alkyl, $C_1-C_4$-alkoxy, phenyl which is unsubstituted or substituted by $C_1-C_4$-alkyl or $C_1-C_4$-alkoxy, or $C_7-C_9$-phenylalkyl which is substituted by $C_1-C_4$-alkyl or $C_1-C_4$-alkoxy, $R^3$ and $R^4$ independently of one another are each hydrogen, $C_1-C_{18}$-alkyl, $C_3-C_{18}$-alkyl which is interrupted by one or more oxygen atoms, $C_1-C_{18}$-alkoxy, $C_4-C_{18}$-alkoxy which is interrupted by one or more oxygen atoms, phenyl which is unsubstituted or substituted by $C_1-C_4$-alkyl or $C_1-C_4$-alkoxy, or phenyl-$C_1-C_8$-alkoxy, $C_1-C_{12}$-C-acylamino, benzoylamino, $C_2-C_{12}$-C-acyloxy or benzoyloxy, n is 0, 1, 2, 3, 4 or 5,

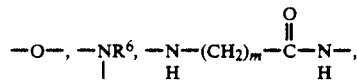

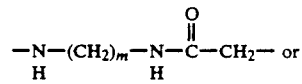

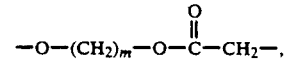

$R^5$ is hydrogen, $C_1-C_8$-alkyl, $C_7-C_{10}$-phenylalkyl, cyanomethyl, aminoethyl, hydroxyethyl, $C_7-C_{10}$-C-acyl or benzoyl, $R^6$ is hydrogen, $C_1-C_8$-alkyl, $C_7-C_{10}$-phenylalkyl or phenyl and m is from 2 to 8, and the acid addition salts and hydrates of this compound.

2. A benzimidazolecarboxanilide as claimed in claim 1, wherein $R^1$ and $R^2$ are each hydrogen.

3. A benzimidazolecarboxanilide as claimed in claim 1, wherein $R^3$ is hydrogen and $R^4$ is hydrogen or ethoxy.

4. A benzimidazolecarboxanilide as claimed in claim 2, wherein $R^3$ is hydrogen and $R^4$ is hydrogen or ethoxy.

5. A benzimidazolecarboxanilide as claimed in claim 1, wherein n is 1 or 2.

6. A benzimidazolecarboxanilide as claimed in claim 2, wherein n is 1 or 2.

7. A benzimidazolecarboxanilide as claimed in claim 3, wherein n is 1 or 2.

8. A benzimidazolecarboxanilide as claimed in claim 4, wherein n is 1 or 2.

9. A benzimidazolecarboxanilide as claimed in claim 1, wherein X is >NH or —NH—CH$_2$—CH$_2$—CO—NH—.

10. A benzimidazolecarboxanilide as claimed in claim 4, wherein X is >NH or —NH—CH$_2$—CH$_2$—CO—NH—.

11. A benzimidazolecarboxanilide as claimed in claim 6, wherein X is >NH or —NH—CH$_2$—CH$_2$—CO—NH—.

12. A benzimidazolecarboxanilide as claimed in claim 7, wherein X is >NH or —NH—CH$_2$—CH$_2$—CO—NH—.

13. A benzimidazolecarboxanilide as claimed in claim 4, wherein $R^5$ is methyl or hydrogen.

14. A benzimidazolecarboxanilide as claimed in claim 6, wherein $R^5$ is methyl or hydrogen.

15. A benzimidazolecarboxanilide as claimed in claim 7, wherein $R^5$ is methyl or hydrogen.

16. A benzimidazolecarboxanilide as claimed in claim 1, wherein $R^5$ is methyl or hydrogen.

17. A stabilized polymeric composition comprising a light and heat stabilizing amount of one or more benzimidazolecarboxanilides as claimed in claim 1 and a polymer.

* * * * *